United States Patent [19]
Springmann et al.

[11] Patent Number: 5,847,263
[45] Date of Patent: Dec. 8, 1998

[54] METHOD AND DEVICE FOR DETERMINING THE MOISTURE CONTENT OF A GAS STREAM

[75] Inventors: Thomas Springmann; Reinhold Münch, both of Freiburg, Germany

[73] Assignee: Testo GmbH & Co., Lenzkirch, Germany

[21] Appl. No.: 869,745

[22] Filed: Jun. 5, 1997

[30] Foreign Application Priority Data

Jun. 5, 1996 [DE] Germany .................. 196 22 530.2

[51] Int. Cl.⁶ .................................................. G01N 25/58
[52] U.S. Cl. ................................... 73/29.01; 374/45
[58] Field of Search .................. 73/29.01, 29.03, 73/25.04; 374/24, 28, 40, 45, 39, 41; 236/44 A; 165/223, 229

[56] References Cited

U.S. PATENT DOCUMENTS

| | | | |
|---|---|---|---|
| 3,229,502 | 1/1966 | Pappas et al. | 73/29.03 |
| 3,265,301 | 8/1966 | Amdur et al. | 73/29.01 X |
| 4,877,329 | 10/1989 | Sauerbaum et al. | 374/28 |
| 5,020,000 | 5/1991 | Carmichael | 73/29.01 X |
| 5,435,146 | 7/1995 | Clark | 73/29.02 X |

FOREIGN PATENT DOCUMENTS

| | | |
|---|---|---|
| 0 541 495 A2 | 5/1993 | European Pat. Off. . |
| 32 24 506 C1 | 7/1983 | Germany . |
| 3224506 C1 | 7/1983 | Germany . |
| 3836496 A1 | 5/1989 | Germany . |
| 4433451 A1 | 3/1996 | Germany . |

*Primary Examiner*—Michael Brock
*Attorney, Agent, or Firm*—Foley, Hoag and Eliot, LLP

[57] ABSTRACT

A method for determining the difference in enthalpy that occurs when a gas stream loaded with water vapor is cooled to a temperature below the dew point temperature, especially for determining its water vapor content (moisture measurement) is disclosed. The device preferably used to perform the method includes a gas cooler having an electrical cooling element and inlet and outlet ports through which a gas stream flows. Measuring devices are provided in the inlet and outlet ports to detect state parameters and through-flow values of the gas stream. The outputs from the measuring devices are evaluated by an evaluation device in connection with the electrical power draw of cooling element to determine the difference in enthalpy between the inlet and outlet ports and/or the water content of the gas stream.

20 Claims, 2 Drawing Sheets

METHOD AND DEVICE FOR DETERMINING THE MOISTURE CONTENT OF A GAS STREAM

FIELD OF THE INVENTION

This invention relates to a method and apparatus for determining the difference in enthalpy that occurs when a gas stream charged with water vapor is cooled to a temperature below the dew point temperature, and especially for determining the water vapor content of the gas stream under such conditions.

BACKGROUND OF THE INVENTION

By measuring the difference in enthalpy of a gas stream charged with water vapor, which occurs when the stream is cooled to a temperature below the dew point temperature, it is possible, using known physical relationships, to determine the water vapor content of the gas stream. This measurement is of great technical significance, for example in gas processing and emission measurement technology, in which the water vapor or moisture content of the gaseous media, for example the flue gas, must be determined in addition to a number of other components.

An example of where it is important to monitor the moisture content of an exhaust gas is disclosed in German Patent Application DE 32 24 506 C1, which relates to the determination of water vapor concentration in exhaust air from tobacco dryers. As shown in DE '506, it is known to supply a sample of gas to be measured to a gas cooler equipped with an electrical cooling element and to condense out approximately the entire water vapor content therein. However, to ensure success, the power of the electrical cooling element must be such that the measured gas stream can be cooled below the dew point temperature under all circumstances in order to ensure complete condensation, even when the gas stream has a high moisture content and a high gas temperature. In this apparatus, the moisture content of the gas stream is determined by feeding a known constant-volume flow of gas to be measured to the gas cooler. In the gas cooler, the stream of gas to be measured is cooled to the point where all of the gases that can be condensed at the preselected temperature, +5° C. for example, condense out. At the gas outlet of the gas cooler, a gas flowmeter is provided to determine the flow rate of the measured gas sample, which is now dry. Using these measurements, the original water vapor content can thus be calculated.

One disadvantageous aspect of this measurement apparatus is the relatively high technical expense, which may be acceptable in fixed applications, such as where the gas stream to be measured stems from a tobacco airstream dryer. However, this expense may be prohibitive for a number of important applications, for example in portable flue gas analyzers like those required for periodic monitoring of heating systems in residences.

Hence, it would be nice to have a method and a device which would economically and reliably enable measure the moisture content of a gas stream using means that are as simple as possible. This is especially true when it is important for the device to be portable, since under these circumstances the device should be compact and of lightweight design.

SUMMARY OF THE INVEION

Applicants discoovered that it would be possible to produce a light weight, portable gas analyzer by measuring the electrical power draw of the cooling element as well as the state and flow characteristics of the gas at the inlet and outlet of the gas cooler. By doing this, the electrical power draw can be used in the calculation of the difference in enthalpy between the inlet and outlet gasses, and thus can be used to determine the water vapor content of the inlet gas stream.

The inventive method and device are suitable not only for individual measurements but also, and particularly, for measurements over a longer period of time, even including permanent monitoring. For this purpose, the changes with time in the state and flow characteristics of the gas stream and/or the electrical power draw of the cooling element are detected and evaluated continuously or sporadically.

There are at least two alternative ways to determine time-wise fluctuations in the difference in enthalpy and/or water vapor content of a gas stream. One way of doing this is to hold the dew point temperature constant at the gas outlet, namely at a value that is below the temperature of the gas stream. The electrical power draw of the cooling element required to keep the temperature constant is detected and the manner in which it changes with time, i.e., its fluctuations, are correlated directly with the time-wise variations in the difference in enthalpy and/or water vapor content.

Alternatively, the electrical power draw of the cooling element is kept constant and the temperature at the gas outlet is measured. In this case, a change in the difference in enthalpy or water vapor content causes a corresponding change in the temperature at the gas outlet, which is continuously or periodically recorded. Of course, the temperature at the gas outlet must always be below the dew point temperature of the gas stream. It is therefore necessary, using the electrical power draw of the cooling element, to lower the temperature at the gas outlet so that the temperature at the outlet never approaches the dew point temperature. Thus, operation of the cooling element should be such that even under extreme conditions, i.e., where the inlet gas temperature is quite high, that the temperature at the gas outlet remains at a safe distance from the dew point temperature.

For calibration, a specific amount of heat is introduced into the gas cooler that corresponds to a specific difference in enthalpy or a specific water vapor content. The reaction of the gas cooler triggered thereby is recorded and evaluated. In this manner, it is possible to obtain a calibration point which accounts for properties associated with the system, such as heat transitions, heat losses, efficiency of the cooling element, aging effects, and the like. A curve can be plotted by multiple sequential repetition of the calibration process for different specific amounts of heat and hence different specific water vapor contents. The number of calibration points required depends primarily on the nature of the calibration curve. In the case of a linear calibration curve, two measurements with different amounts of heat are sufficient, with accuracy being increased by further calibration measurements. In extreme cases, one calibration point can suffice.

To add the amount of heat desired, gas streams can be used with precisely known state values, especially with known enthalpy and/or water vapor content, that are supplied to the gas cooler. In this manner, extremely precise calibration is possible.

Alternatively, and preferably, a specific amount of heat can be added by using a heating element integrated into the gas cooler. By doing this, it is possible to simulate differences in enthalpy or water vapor content without requiring a calibration gas stream to be provided. Calibration can thus take place internally, theoretically even during long-term measurements, for which purpose only brief interruptions in the measurements are required.

A device suitable for this purpose can be built by taking a known gas cooler with an electrical cooling element, and providing it with measuring devices in the vicinity of gas inlet and gas outlet ports to detect the state parameters and through-flow values of the gas stream, for example temperature, pressure, and flow volume. Additionally, a measuring device may be provided to measure the electrical power draw of the cooling element. Using an evaluation unit, such as a microprocessor, the electrical power draw of the cooling element can be used in connection with the state parameters and the through-flow values of the gas stream at the gas outlet and gas inlet to determine the moisture content of the gas stream.

In most applications, the gas cooler should have a condensate separator to prepare the gas for measurement as the outlet stream of gas. One preferred type of gas cooling element is a Peltier effect element, which does not require any moving parts and therefore requires little maintenance and is insensitive to contamination. This aspect is particularly important in flue gas analysis, since the particles of soot and dust present under these conditions produce a high degree of contamination. In addition, aggressive components are present in the flue gas, such as chlorine or fluorine, against which sufficient protection must be provided. Finally, the gas to be measured, as a rule, is at a high temperature that sometimes can be as high as 1500° C. Since a Peltier effect element is robust, the inventive device has considerable advantages over other concepts and allows measurements even under extreme conditions because of its simple and sturdy design.

Preferably, a heating element is integrated into the gas cooler in order to permit simple calibration. A heating cartridge is especially suited for this purpose, and is particularly simple to integrate into the gas cooler because of its compact design.

It has been shown to be advantageous in practice to make the heating power of the heating element adjustable in several stages, with each stage representing an exactly reproducible heating power. For the specific application of a portable flue gas analyzer, it has proven to be advantageous to use a heating cartridge whose power can be adjusted in the range from 1.0 W to 15 W in five stages. In this way, dew point temperatures in the gas cooler between approximately 10° C. and 80° C. can be simulated. Self-calibration of the system is thus possible with minimum expense.

BRIEF DESCRIPTION OF THE FIGURES

The preferred embodiments of the present invention will now be described more specifically with reference to the attached drawings, wherein.

DETAILED DESCRIPTION OF THE PREFERRED EMBODIMENTS

Figure 1:
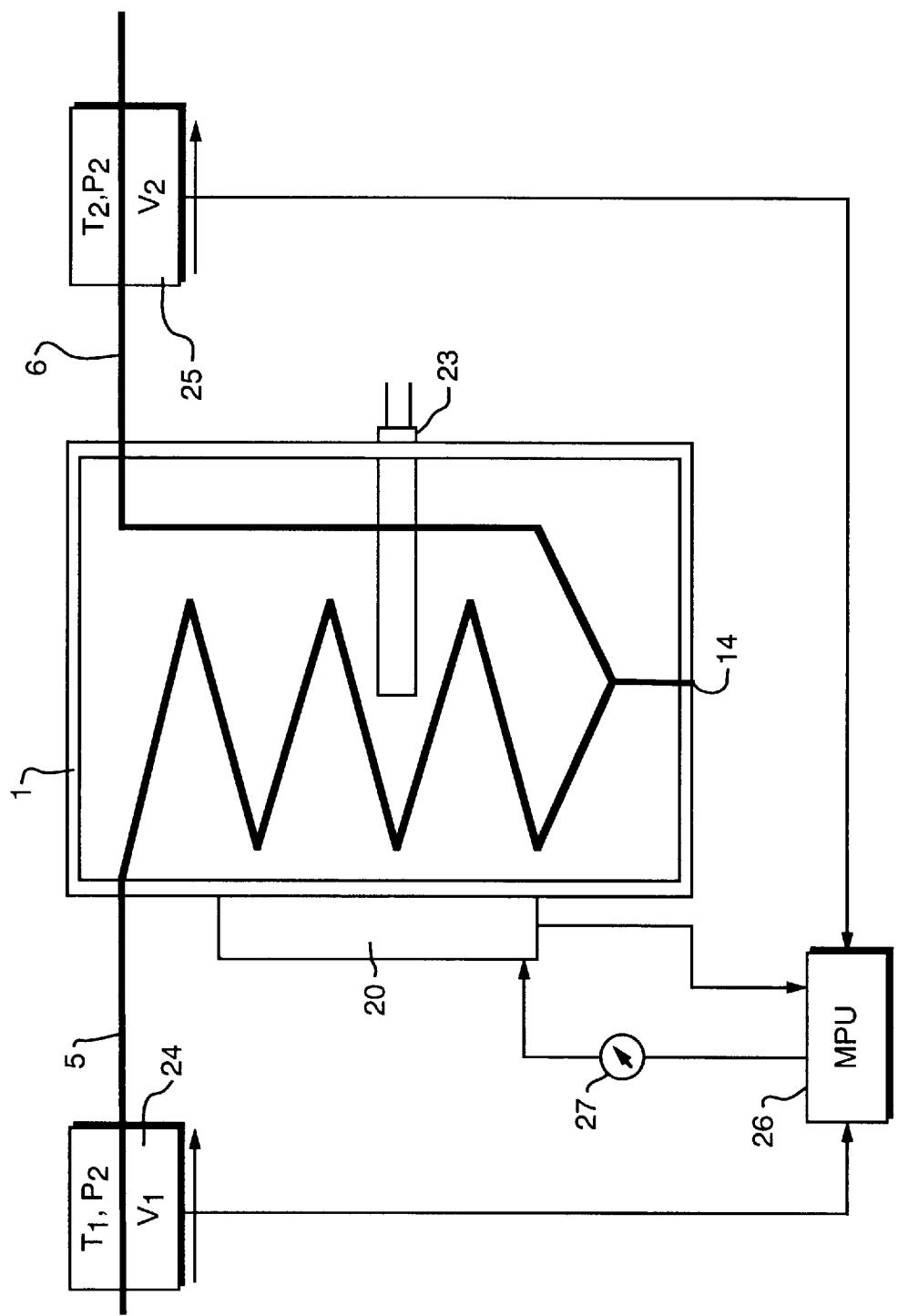
FIG. 1 is a view of the general design of the device.

As shown in FIG. 1, a continuously tapped measured gas stream is conducted through a gas feed pipe 5 to a gas cooler 1. State parameter measurement devices 24 are provided in the vicinity of the gas feed pipe 5, which are used to measure state parameters and through-flow values for the measured gas stream, for example temperature T1, pressure P1, and/or flow volume V1. These measured values are then supplied to an evaluation unit 26, which preferably is a microprocessor unit.

The measured gas stream is conducted through gas cooler 1 and cooled. For this purpose, a Peltier effect element 20 is provided in gas cooler 1. The electrical power draw of the Peltier effect element 20 is measured using an appropriate meter 27 and the output of the measurement is provided to the evaluation unit 26.

The gas stream is cooled to a temperature below the dew point temperature as it passes through gas cooler 1. As a result, the water vapor condenses to form condensate (water) that leaves gas cooler 1 through a condensate line 14. The remaining dry gas leaves gas cooler 1 through the gas outlet pipe 6, whereupon, by means of measuring devices 25, the state and through-flow parameters, for example temperature T2, pressure P2, or volume flow V2, are measured and supplied to the evaluation unit 26.

In one embodiment, the Peltier effect element 20 is regulated by the evaluation unit 26 so that the temperature of the gas stream at the outlet is kept at a constant level. The difference in enthalpy or water vapor content determined in the evaluation unit from the state and through-flow parameters can be subject to fluctuations. In the case where the temperature of the gas stream at the outlet is maintained at a constant level, this fluctuation in difference in enthalpy or water vapor content manifests itself as a change in the required cooling power over time.

In another embodiment, the Peltier effect element 20 is maintained at a constant level and the temperature of the gas stream at the outlet is kept at a constant level. In this situation, the fluctuations of the state and flow-through parameters are monitored to detect changes in the difference in enthalpy or water vapor. By using a stable power supply for the Peltier effect element, it may thus be possible to eliminate the need for meter 27.

For calibration, a heating element, such as a heating cartridge 23, is integrated into gas cooler 1. In operation, the measured gas stream is interrupted and a specific amount of heat is added to gas cooler 1 by heating cartridge 23. The response of the gas cooler 1 is recorded and used to form a calibration curve. A complete calibration curve is typically plotted using several calibration points. Operation of the heating element can be controlled by the evaluation unit 26.

Figure 2:
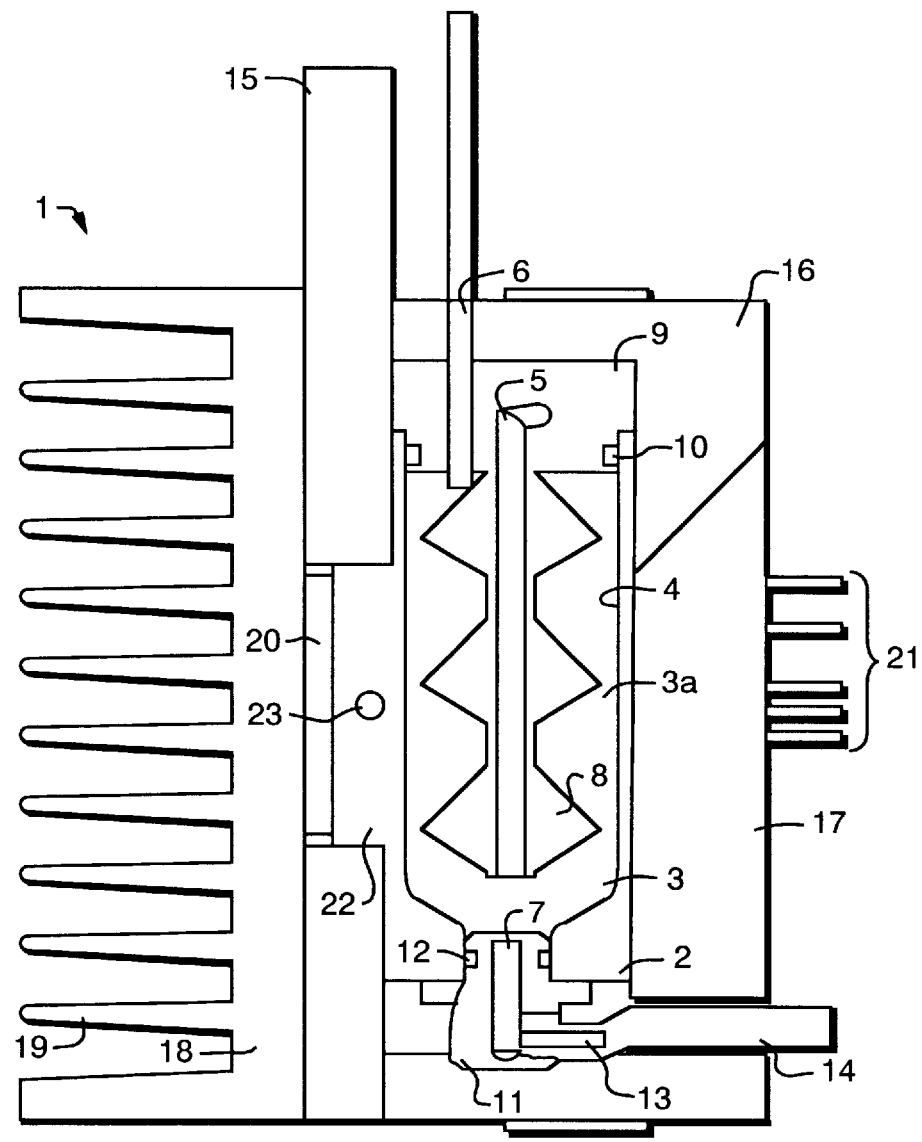
FIG. 2 is a cut away view of a modified gas cooler according to the invention.

A more detailed view of a preferred embodiment is illustrated in FIG. 2.

As shown in FIG. 2, a cooling block 2 is externally cooled by a Peltier effect element 20. Peltier effect element 20 is connected in a known manner by electrical leads 21 to an evaluation device 26 (see FIG. 1). Peltier effect element 20 is in flush contact with cooling block 2 on its cold side and in flush contact with a cooling strip 18 on its warm side. For optimum delivery of heat to the environment, cooling strip 18 has a plurality of cooling fins 19.

Cooling block 2 has the basic shape of a vertically mounted right parallelepiped with a rectangular base. It has a recess 3 that is cylindrical and runs vertically. The recess makes a transition at its lower end to a conical section and is continued upward. Recess 3 is closed by a plug 9 at the top. An elastically flexible sealing ring 10 is provided at the junction between the plug 9 and the recess 3 to provide a gas-tight seal between plug 9 and cooling block 2 at the upper end of recess 3.

A gas feed pipe 5 is guided through plug 9 and terminates coaxially at the top of plug 9 in recess 3. The gas feed pipe 5 extends up to the vicinity of the lower end of recess 3 so that an annular space 3a is formed between gas feed pipe 5 and the wall of recess 3. A gas outlet pipe 6 terminates in the vicinity of annular space 3a. Gas outlet pipe 6 is likewise located in plug 9. It passes through plug 9 in an axial direction and projects outward above plug 9 at least far enough so that a connecting element, not shown here in greater detail, for example in the form of a hose coupling, can be attached or a hose can be pushed directly onto it. Gas feed pipe 5 in the present case is guided essentially radially outward through plug 9 and projects beyond the plug in a manner similar to gas outlet pipe 6 in order to permit connection to a line that conducts the gas to be measured, for example to a heatable measuring gas tube with a dip tube.

Gas feed pipe 5 has a plurality of vorticizing elements 8 in the vicinity of the recess 3. These are in the shape of frustra of cones that are arranged pair wise and coaxially with respect to one another. In the embodiment shown, three such double cone frustra arrangements are provided. This creates a situation in which the gas flowing upward in annular space 3a cannot form an orderly tubular flow. The multiple sequence of narrowed cross sections and expanded cross sections produces powerful vortices that considerably improve heat transfer between the gas and the wall.

Gas feed pipe 5 including vorticizing elements 8 mounted on it is permanently connected to plug 9. In this way, the surfaces of vorticizing elements 9 in particular can be cleaned in a simple fashion. Advantageously, these components are integrated in the form of plastic injection-molded parts. Vorticizing elements 8 and plug 9 can also be made in the form of turned parts.

Coating 4 on the wall of recess 3 is particularly important. A suitable choice of material and coating thickness provides assurance that the wall of cooling block 2 is reliably protected in the area exposed to the gas without heat transfer being adversely affected significantly. A suitable material for coating 4 has been found to be a plastic such as RILSAN® or TEFLON® for example, applied in thicknesses of about 300 $\mu$m. These materials are inert to the aggressive components of the gas and have a sufficient adhesive property, especially with respect to aluminum, which is the preferred material for cooling block 2. A coating thickness of this order of magnitude, for the materials mentioned above and those comparable therewith, guarantees excellent heat conductivity so that outstanding efficiency can be achieved for the entire gas cooler.

The lower end of recess 3 is made tapered or conical so that the drops of condensate that run down the walls can flow out through opening 7 located at the lowest point in recess 3. Opening 7 serves to carry away the condensate and can be designed in a well known manner. In the embodiment shown, opening 7 is not made directly as a hole in cooling block 2 but in the form of a hole made in plug 11. A stub 13 is mounted on plug 11 and extends radially. In this instance, the stub terminates in a bore and receives condensate line 14 that leads to the outside. Plug 11 is sealed to cooling element 2 with an elastically flexible seal 12.

Cooling block 2 is essentially completely surrounded by an insulating jacket which, in the illustrated example, includes three individual parts. A partition 15 separates cooling block 2 from cooling strip 18. Partition 15 has a recess in the vicinity of the Peltier effect element 20, into which recess a shoulder-like projection 22 of cooling block 2 projects to form a contact area with the cold side of Peltier effect element 20.

Additional insulating elements surround cooling block 2 on the other sides. Lower part of insulating jacket 17 is traversed by condensate line 14 and connecting leads 21 of Peltier effect element 20. Upper part of insulating jacket 16 is designed so that it can be readily removed in order to withdraw plug 9 from cooling block 2 for cleaning.

Insulating jacket 15, 16, 17 further improves the efficiency of the gas cooler since it largely suppresses the transfer of heat from cooling block 2 to the environment.

A heating cartridge 23 is preferably located inside gas cooler 1, and is used for the calibration process described in greater detail above.

From the foregoing description it will be apparent that a commercial gas cooler can be provided which is capable of determining the moisture content and/or enthalpy of a gas stream. This gas cooler uses conventional temperature and pressure sensors and flow meters which can be easily mounted in the vicinity of the gas inlet and gas outlet area. Electrical signals produced by these conventional temperature, pressure and flow sensors are input to the evaluation unit 26, such as a microprocessor, to determine the moisture content and/or enthalpy of the gas stream.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

This application claims priority from German Application No. 196 22 530.2-52, the content of which is hereby incorporated by reference.

What is claim is:

1. A device for determining the water vapor content of a gas stream, comprising:

a gas cooler having an electrical cooling element; and an evaluation device in which an electrical power draw of the cooling element is used in connection with detected properties of the gas stream upstream of the gas cooler and downstream of the gas cooler to determine the water vapor content of the gas stream.

2. The device of claim 1, wherein the gas cooler has inlet and outlet openings to accept at least a portion of a gas stream flowing thereby.

3. The device of claim 2, wherein the gas stream is received at the inlet opening, flows through the gas cooler, and exits the gas cooler through the outlet opening.

4. The device of claim 2, further comprising:

measuring devices provided in the vicinity of the inlet and outlet openings to detect said properties of the gas stream upstream of the gas cooler and downstream of the gas cooler.

5. The device of claim 2, further comprising:

a measuring device to detect an electrical power draw of the cooling element.

6. A method for determining the difference in enthalpy that occurs when a gas stream loaded with water vapor is cooled to a temperature below the dew point temperature, comprising:

using a gas cooler with an electrical cooling element to reduce the temperature of at least a portion of the gas stream, measuring properties of the at least a portion of the gas stream upstream and downstream of the gas cooler;

sensing an amount of electrical power used by the electrical cooling element to reduce the temperature of the at least a portion of the gas stream; and using the sensed amount of electrical power, in connection with the measured properties of the gas stream, to determine the difference in enthalpy between the inlet gas stream and outlet gas stream.

7. The method of claim 6, wherein the difference in enthalpy between the inlet gas stream and the outlet gas stream is correlated to the moisture content of the gas stream.

8. The method according to claim 6, wherein the measured gas stream properties include temperature, pressure and flow rate of the gas stream, and wherein an electrical power draw of the cooling element is sensed as the amount of electrical power used by the cooling element.

9. A method according to claim 8, wherein the difference in enthalpy between the inlet gas stream and outlet gas stream is ascertained by maintaining the outlet gas temperature at a constant value and monitoring the electrical power draw of the electrical cooling element.

10. A method according to claim 8, wherein the difference in enthalpy between the inlet gas stream and outlet gas stream is ascertained by maintaining a near constant supply of power to the electrical cooling element and measuring fluctuations in temperature of the outlet gas stream.

11. A method according to claim 6, wherein calibration of the process is conducted by injecting a quantity of heat into the gas cooler and monitoring the behavior of the electronic gas cooler.

12. The method according to claim 11, wherein the quantity of heat is predetermined to correspond to one of a specific difference in enthalpy and a specific water vapor content.

13. A method according to claim 6, wherein gas streams with one of known state parameters and known water vapor contents are used for calibration.

14. A gas cooler for determining one of the difference in enthalpy which occurs when a gas stream loaded with water vapor is cooled to a temperature below its dew point temperature, and the water vapor content of the gas stream, comprising:

a gas cooler having an inlet port for receiving a gas stream and an outlet port for outputting a gas stream, a condensate port for discharging condensate, and an electrical cooling element the power draw of which is capable of being monitored, at least one measuring device provided in the vicinity of the inlet port to detect state parameters of the inlet gas stream;

at least one measuring device provided in the vicinity of the outlet port to detect state parameters of the outlet gas stream;

a measuring device to detect an electrical power draw of the cooling element, and an evaluation device in which the measured electrical power draw is used in connection with the detected state parameters at the inlet port and outlet port to evaluate at least one of the difference in enthalpy between the inlet port and the outlet port, and the water vapor content of the gas stream.

15. A device according to claim 14, wherein the cooling element is a Peltier element.

16. A device according to claim 14, further comprising a heating element integrated into the gas cooler.

17. A device according to claim 16, wherein the heating element is a heating cartridge.

18. A device according to claim 16, wherein the heating power of the heating element can be adjusted in a plurality of stages.

19. A device according to claim 18, wherein the heating power can be adjusted between 1.0 W and 15 W.

20. A device according to claim 14, wherein the state parameters detected at each of the inlet and outlet ports include the temperature of the gas stream at the inlet port and the outlet port, the pressure of the gas stream at the inlet port and outlet port, and the flow of the gas stream at the inlet port and the outlet port.

* * * * *